United States Patent [19]

Marandos

[11] Patent Number: 5,400,787
[45] Date of Patent: Mar. 28, 1995

[54] INFLATABLE MAGNETIC RESONANCE IMAGING SENSING COIL ASSEMBLY POSITIONING AND RETAINING DEVICE AND METHOD FOR USING THE SAME

[75] Inventor: Thomas A. Marandos, Commack, N.Y.

[73] Assignee: Magna-Lab, Inc., Hicksville, N.Y.

[21] Appl. No.: 157,984

[22] Filed: Nov. 24, 1993

[51] Int. Cl.⁶ ............................................. A61B 5/055
[52] U.S. Cl. ................................. 128/653.5; 324/318
[58] Field of Search .......................... 128/653.2, 653.5; 607/50, 51; 324/318, 322

[56] References Cited

U.S. PATENT DOCUMENTS 4,398,149  8/1983  Zens .
4,791,372 12/1988  Kirk et al. .
4,793,356 12/1988  Misic et al. .
4,887,038 12/1989  Vortruba et al. .

FOREIGN PATENT DOCUMENTS 0385367  9/1990  European Pat. Off. ......... 128/653.5
61-59806  3/1986  Japan .
4332531 11/1992  Japan ............................... 128/653.5
5076509  3/1993  Japan ............................... 128/653.5

*Primary Examiner*—Ruth S. Smith
*Attorney, Agent, or Firm*—Darby & Darby

[57] ABSTRACT

An inflatable coil positioning device includes a coil, a first inflatable sleeve disposed radially about the coil and a second inflatable sleeve disposed radially within the coil. The first inflatable sleeve and the second inflatable sleeve each include at least two sections. The coil is placed about a target section of the patient to be imaged. The second inflatable sleeve is inflated until the coil is securely mounted on the target section. The mounted coil and target section of the patient are then placed within a predetermined section of a nuclear magnetic resonance imaging magnet. The first inflatable sleeve is inflated until the mounted coil and target section of the patient are securely retained within the predetermined section of the magnet.

21 Claims, 3 Drawing Sheets

INFLATABLE MAGNETIC RESONANCE IMAGING SENSING COIL ASSEMBLY POSITIONING AND RETAINING DEVICE AND METHOD FOR USING THE SAME

FIELD OF THE INVENTION

The present invention relates generally to a device for positioning a sensing coil assembly that is placed about a patient's body part within a magnet of a nuclear magnetic resonance imaging machine. More specifically, the present invention relates to an inflatable positioning device for a sensing coil assembly that has an inflatable chamber radially within the coil to position the coil with respect to the patient and an inflatable chamber radially outside of the coil to position the coil with respect to the magnet.

BACKGROUND OF THE INVENTION

Sensing coil assemblies are necessary in nuclear magnetic resonance imaging (NMRI) apparatus to produce an image. Such sensing coil assemblies may be placed around a body part of the patient to be imaged, such as an arm or leg. Frequently, a significant void or empty region occurs between the coil and the body part to be imaged as well as between the coil and the inner surfaces of the magnet when the body part is placed within the magnet. Technicians will frequently fill those voids with loose pieces of foam or other available material to position the coil about the portion of the patient to be imaged as well as to position the coil between the poles of the magnet. Accordingly, the technicians first pack loose foam between the section of the body to be imaged and the coil. Then the technician will place the foam packed coil and section of the body within a gap between two poles of the magnet. The area between the coil and the magnet poles is then packed with more foam until the desired position is achieved. The technician will then take a quick image to ensure that the body section and coil are properly positioned. If the image is not clear, the entire procedure is repeated until the body section and coil are properly positioned within the magnet gap.

Notwithstanding the use of loose pieces of foam to help position the coil, there are still major problems involved. Patients frequently unintentionally move during the imaging process. This accidental movement causes the patient to move from the preferred imaging position, resulting in an unacceptable image.

It is, therefore, an object of the present invention to provide a positioning device for an NMRI sensing coil assembly that properly positions the body part of the patient to be imaged within the coil and properly positions the coil between the poles of the magnet, while simultaneously preventing the patient from accidentally moving the body part during the NMRI process.

It is yet another object of the present invention to provide an inflatable NMRI sensing coil positioning device that requires fewer parts and, thus, is smaller and easier to manufacture. It is still a further object of the present invention that the inflatable NMRI sensing coil positioning device be simple and cost efficient to manufacture, yet be reliable and efficient in use.

SUMMARY OF THE INVENTION

In accordance with a preferred embodiment demonstrating further objects, features and advantages of the invention, an inflatable NMRI sensing coil assembly positioning device includes a first inflatable chamber disposed radially outwardly of the coil and a second inflatable chamber coil disposed radially inwardly of the coil. The first and second inflatable chambers each comprise at least two sections.

BRIEF DESCRIPTION OF THE DRAWINGS

The above and still further objects, features and advantages of the present invention will become apparent upon consideration of the following detailed description of a presently preferred exemplary embodiment thereof, especially when taken in conjunction with the accompanying drawings wherein like reference numerals in the various figures are utilized to designate like components, and wherein.

DETAILED DESCRIPTION OF THE PRESENTLY PREFERRED EMBODIMENTS

Figure 1:
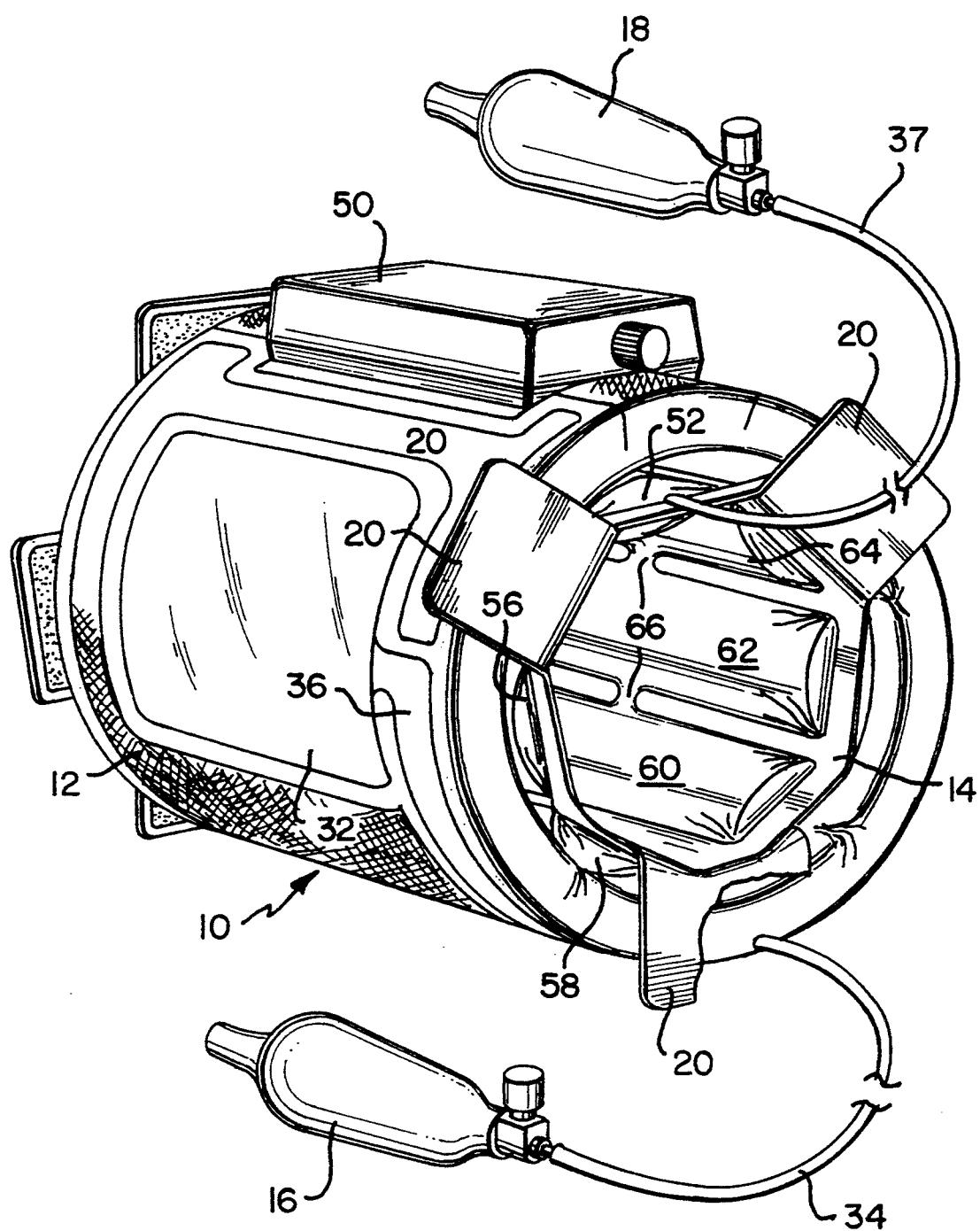
FIG. 1 is a perspective view of an NMRI sensing coil assembly positioning device according to the present invention having a first inflatable chamber disposed about the coil and a second inflatable chamber disposed radially inwardly of the coil.
Figure 3:
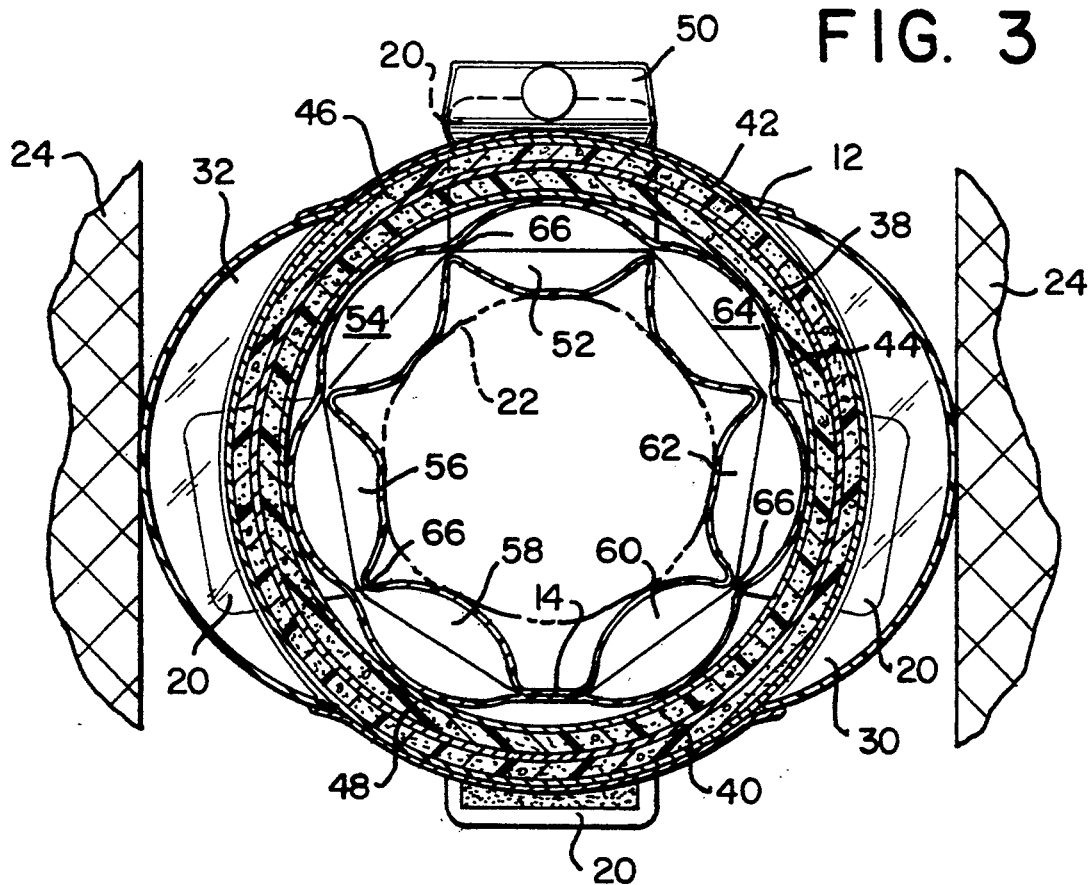
FIG. 3 is a cross-sectional view taken along lines 3—3 of FIG. 2 and looking in the direction of the arrows.
Figure 4:
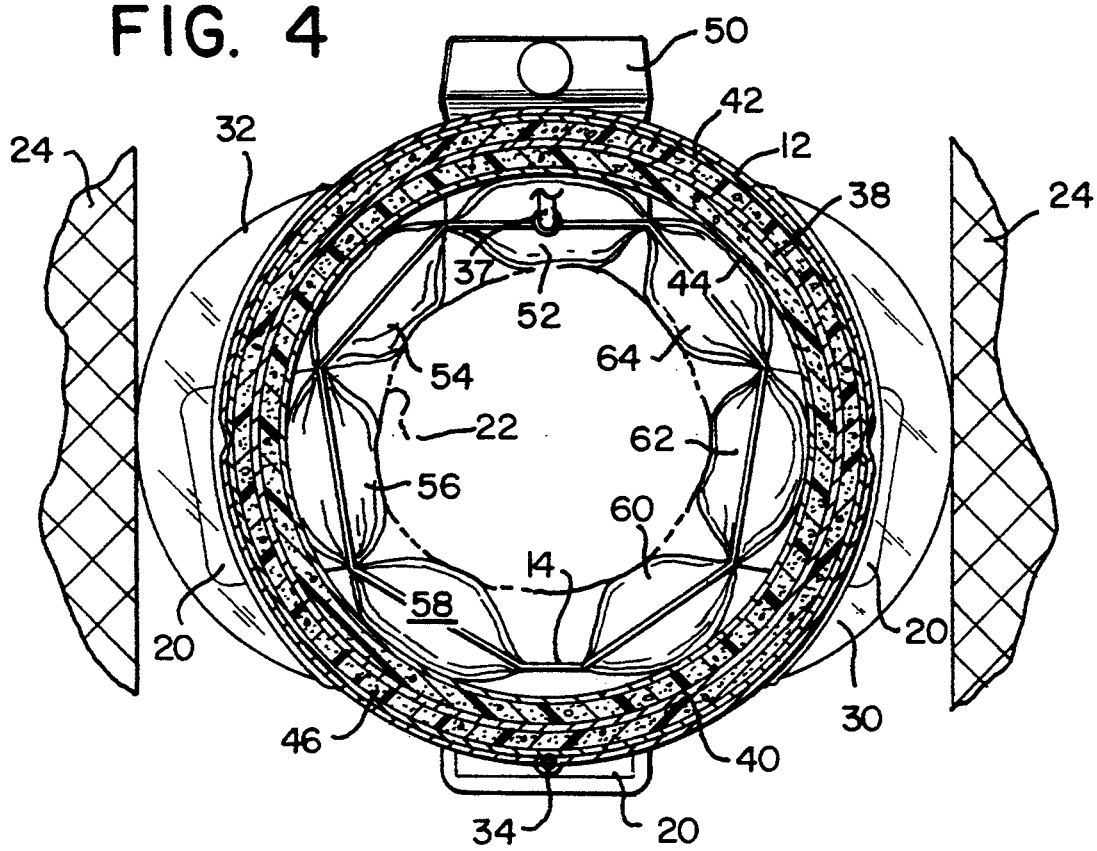
FIG. 4 is a cross-sectional view taken along lines 4—4 of FIG. 2 and looking in the direction of the arrows.

Referring to FIG. 1, an inflatable coil positioning device 10 for magnetic resonance imaging (MRI) is illustrated. The inflatable coil positioning device 10 includes a first inflatable sleeve 12 disposed radially about a sensing coil assembly 38 (see FIG. 3) and a second inflatable sleeve 14 disposed radially inward of the sensing coil assembly. An inflation bulb 16, 18, of the type conventionally used for taking blood pressure with a sphygmomanometer cuff, are used to inflate and deflate the first inflatable sleeve 12 and the second inflatable sleeve 14, respectively. The second inflatable sleeve 14 is detachably retained within the coil by the use of complementary hook and loop type fastener material disposed on the under surface of tabs 20. The second bladder 14 can be attached by other means, such as snaps, removable rivets, etc.

Figure 2:
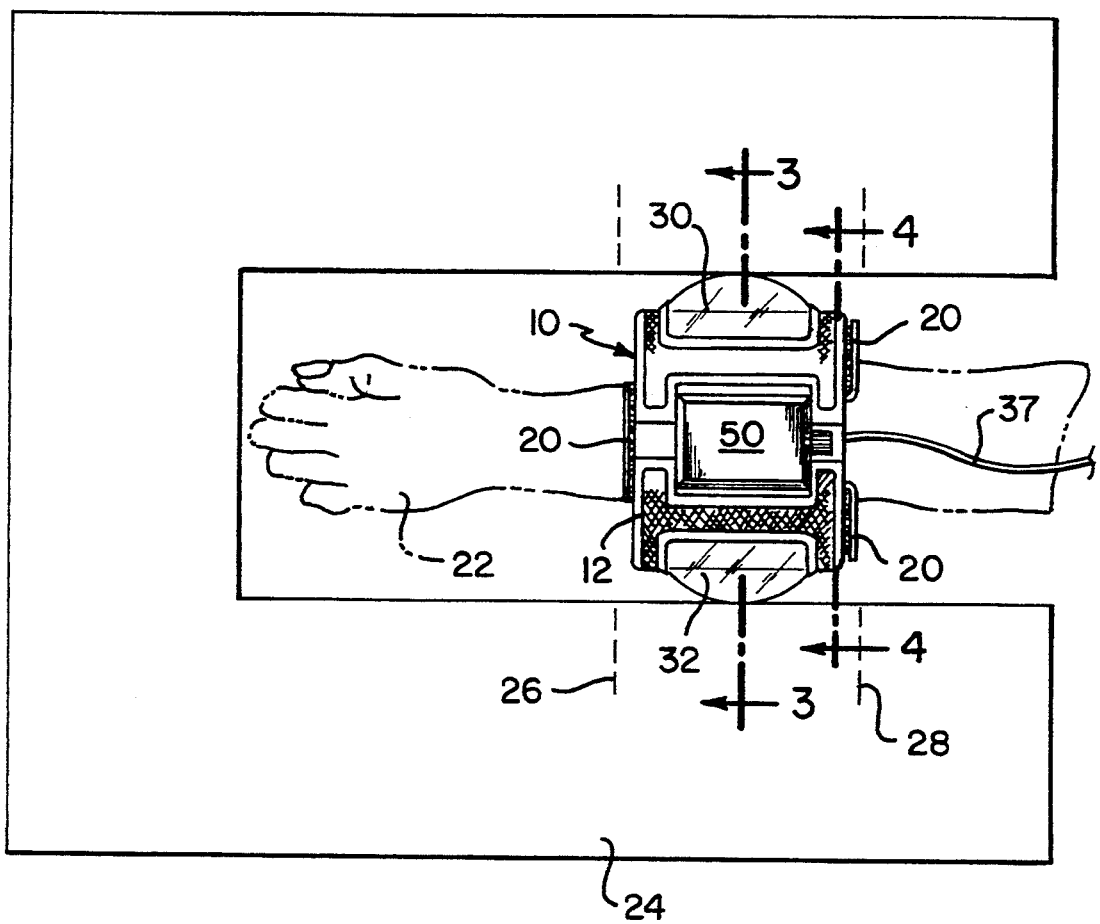
FIG. 2 is a plan view of the inflatable coil positioning device of FIG. 1 placed about the arm of a patient and within a magnet.

Referring now to FIG. 2, the inflatable coil positioning device 10 is shown attached to an arm 22 of a patient and within an MRI magnet 24 of a magnetic resonance imaging machine. Some magnets have a marked "sweet-spot", indicated as being between reference lines 26 and 28, which is located where the magnetic field is the strongest and most uniform. Of course, it is preferred that the device 10 be positioned within the sweet-spot of the magnet 24.

The first inflatable sleeve 12, which is detachably disposed radially about the coil 38, includes two diametrically opposed inflatable sections 30, 32 that are in fluid communication with one another. These sections 30, 32 are inflated with inflation bulb 16, which is in fluid communication therewith via a conduit 34 and an arcuate passageway 36 (See FIG. 1). Alternatively, the first sleeve 12 can be comprised of only one section or any number of sections.

The second inflatable sleeve 14, disposed radially inward of the coil 38, is inflated with inflation bulb 18, which is in fluid communication therewith via a conduit 37. Coil 38 may be a known type of device, see for example, Kirk et al. U.S. Pat. No. 4,791,372, or Misic et al. U.S. Pat. No. 4,793,356, the disclosures of which are hereby incorporated by reference. The coil 38 is coupled to a firm cylindrical sleeve 40 (see FIG. 3). In one embodiment sleeve 40 is made of a G10 fiberglass sheet having a thickness of 0.03 inches.

A second firm sleeve 42 is disposed radially about the first sleeve 40 and coil 38, and radially within the first inflatable sleeve 12. A third firm sleeve 44 is disposed radially within the coil 38 and first sleeve 40, and radially about the second inflatable sleeve 14. In one embodiment the second sleeve 42 and the third sleeve 44 are also made of a G10 fiberglass sheet having a thickness of 0.03 inches. A sleeve of foam material 46 is disposed between the coil 38 and sleeve 40, and the second sleeve 42. Another sleeve of foam material 48 is disposed between the coil 38 and first sleeve 40, and the third sleeve 44. In one embodiment the foam is a velora foam having a thickness of 0.25 inches. The electronics associated with operating coil 38 are disposed on the cylindrical outer surface of the second sleeve 42 within a housing 50 and communicate electrically with coil 38 in a known manner.

The second inflatable sleeve 14, disposed radially within the coil, is illustrated as having seven sections 52, 54, 56, 58, 60, 62 and 64. Each section of the second inflatable sleeve 14 communicates with an adjacent sleeve through a passageway 66. Alternatively, a plurality of passageways could be provided between adjacent sections of the second inflatable sleeve 14. Alternatively, the second sleeve 14 can be comprised of only one section. Additionally, the second inflatable sleeve 14 may be comprised of any number of sections, preferably an even number to evenly support the arm 22 or other portion of the body being imaged.

The use of the inflatable coil positioning device 10 will be described below with reference to FIGS. 1-4. The inflatable coil positioning device 10 is first placed about a so called "target section" of the patient to be imaged by MRI. For example, as illustrated in FIG. 2, the device 10 is attached about the arm 22 of a patient. The second inflatable sleeve 14, disposed radially within the coil 38, is then inflated by use of inflation bulb 18 until the device 10 is firmly mounted on the target section of the patient. The mounted inflatable coil device 10 and the target section of the patient are then positioned within the predetermined sweet-spot of magnet 24.

Device 10 is aligned within magnet 24, between reference lines 26, 28, such that sections 30, 32 of sleeve 12 are adjacent to the poles of the magnet 24. Sleeve 12 is then inflated by using inflation bulb 16 until the device 10 is firmly retained within to the magnet 24 at its sweet-spot. The two sections 30, 32 of the inflatable sleeve 12 are inflated until the device 10 is adequately positioned between the two poles of the magnet 24. In practice, the portions of the sections 30, 32 that contact the poles of the magnet 24 will flatten to a greater degree than illustrated to form a planer contact surface between the poles of the magnet and sections 30, 32. By following this procedure, the target section of the patient to be imaged is positioned coaxial within coil 38 and is centered within the gap between the two poles of the magnet 24.

It will be appreciated that the inflatable coil positioning device of the present invention successfully positions the target section of the body coaxial within the coil and centered within the gap of the magnet. Moreover, successful positioning can be expected upon the first attempt every time. By eliminating the trial and error procedure necessary with existing positioning devices, the present invention substantially decreases the time required for MRI examination of a patient. This would permit more patients to be examined in the course of a day, leading to a reduced cost to the patient.

From the foregoing description, it will be appreciated that the present invention makes available a compact, cost efficient coil positioning device. The inflatable coil positioning device is designed to allow for simple, efficient operation, while preventing the patient from inadvertently moving with respect to the coil and the magnet.

Having described the presently preferred exemplary embodiment of a new and improved inflatable coil positioning device and method of using the same in accordance with the present invention, it is intended that the other modifications, variations and changes will be suggested to those skilled in the art in view of the teaching set forth herein. It is, therefore, to be understood that all such variations, modifications, and changes are intended to fall within the scope of the present invention as defined by the appended claims.

What I claim is:

1. An MRI coil assembly comprising:
   a coil;
   a first inflatable sleeve disposed radially about said coil and having at least one section;
   a second sleeve disposed radially within said coil and having at least one inflatable section said second sleeve having means for positioning said coil about a target section of a patient such that said target section is radially within said second sleeve.

2. The apparatus according to claim 1, wherein said first inflatable sleeve includes two sections that are diametrically opposite one another.

3. The apparatus according to claim 2, wherein said two sections of said first inflatable sleeve are in fluid communication with each other, said second sleeve includes at least two sections that are in fluid communication with each other.

4. The apparatus according to claim 1, further including a first firm sleeve, said coil being mounted on said first firm sleeve.

5. The apparatus according to claim 4, further including a second firm sleeve disposed radially about said coil and radially within said first inflatable sleeve.

6. The apparatus according to claim 5, further including a third firm sleeve disposed radially within said coil and radially about said second sleeve.

7. The apparatus according to claim 6, wherein said first, second and third firm sleeves comprise a rigid plastic material.

8. The apparatus according to claim 6, further including a first flexible sleeve of foam material disposed between said coil and said second firm sleeve.

9. The apparatus according to claim 8, further including a second flexible sleeve of foam material being disposed between said coil and said third firm sleeve.

10. A method of positioning a coil about a patient and within a magnet for magnetic resonance imaging comprising the steps of:
   mounting the coil in a housing having first and second inflatable sleeves disposed radially outward and inward of the housing;

placing the housing about a target section of the patient to be imaged;

inflating the second inflatable sleeve to firmly mount the coil to said target section;

placing said mounted coil and said target section of said patient within a predetermined section of said magnet; and inflating said first inflatable sleeve until said mounted coil and said target section of said patient are firmly secured within the predetermined section of said magnet.

11. The method according to claim 10, further comprising the step of placing said target section of said patient coaxial to the coil.

12. The method according to claim 11, wherein the magnet comprises a pair of spaced apart poles having a gap therebetween, further comprising the step of placing the coil such that it is centered within the gap of the magnet.

13. The method according to claim 12, wherein the first inflatable sleeve comprises at least two sections, further comprising the step of inflating said first inflatable sleeve to contact said patient, the second inflatable sleeve comprises at least two sections, inflating said second inflatable sleeve to contact said magnet.

14. The method according to claim 13, further comprising the step of placing two of said at least two sections of said first inflatable sleeve diametrically opposite one another.

15. The method according to claim 14, further comprising the step of placing said at least two sections of said first inflatable sleeve in fluid communication with each other, and placing said at least two sections of said second inflatable sleeve in fluid communication with each other.

16. The method according to claim 13, wherein said housing includes a first sleeve, further including the step of coupling said coil to said first sleeve.

17. The method according to claim 16, wherein said housing includes a second sleeve, further including a step of disposing a second sleeve radially about said coil and radially within said first inflatable sleeve.

18. The method according to claim 17, wherein said housing includes a third sleeve, further including a step of disposing said third sleeve radially within said coil and radially about said second inflatable sleeve.

19. The method according to claim 18, wherein said housing includes a fourth sleeve, further including a step of disposing said fourth sleeve of foam material between said coil and said second sleeve.

20. The method according to claim 19, wherein said housing includes a fifth sleeve, further including a step of disposing said fifth sleeve of foam material between said coil and said third sleeve.

21. The method according to claim 20, further including a step of communicating electronically with said coil.

* * * * *